United States Patent [19]

Van Ee

[11] Patent Number: 5,024,943

[45] Date of Patent: Jun. 18, 1991

[54] REGULATORY REGION CLONING AND ANALYSIS PLASMID FOR BACILLUS

[75] Inventor: Jan H. Van Ee, Nieuwerkerk a/d Ijssel, Netherlands

[73] Assignee: Gist-brocades, Delft, Netherlands

[21] Appl. No.: 927,249

[22] Filed: Nov. 4, 1986

[30] Foreign Application Priority Data

Nov. 7, 1985 [NL] Netherlands ............... 8503074

[51] Int. Cl.$^5$ .................. C12N 15/00; C12N 1/20
[52] U.S. Cl. ..................... 435/172.3; 435/252.31; 435/320.1; 435/832; 536/27; 935/8; 935/9; 935/29; 935/41; 935/45; 935/48; 935/61; 935/74; 935/76
[58] Field of Search ............ 435/68, 91, 170, 172, 435/172.3, 252.31, 320, 822, 832, 839; 536/27; 935/6, 8, 9, 10, 22, 23, 24, 27, 29, 33, 38, 39, 41, 44, 45, 46, 47, 48, 60, 61, 74

[56] References Cited

U.S. PATENT DOCUMENTS 4,624,926 11/1986 Inouye et al. .................. 435/253
4,711,843 12/1987 Chang ............................. 435/68

FOREIGN PATENT DOCUMENTS 2091268 7/1982 United Kingdom ............. 435/172.3

OTHER PUBLICATIONS

Mongkolsuk et al., 1983, J. Bacteriol 155(3):1399–1406.
Palva et al., 1981, Gene 15:43–51.
Stanssens et al., 1985 36:211–223.
Williams et al., 1981 *J. Bacteriol* 146:1162.
Ortlepp et al., 1983, *Gene*, 23:267.
Enger-Valk et al., 1981, *Gene*, 15:297.
Moran, et al., 1982, *MGG*, 186:339.
Gryezan et al., 1978, *J Bacteriol*, 134:318.
Moran et al., 1981, *Cell*, 25:783.

*Primary Examiner*—Thomas G. Wiseman
*Assistant Examiner*—Richard C. Peat
*Attorney, Agent, or Firm*—Bertram I. Rowland; Barbara Rae-Venter

[57] ABSTRACT

Novel constructs in plasmids are provided for evaluating the efficiency of expression and secretion of structural genes. The constructs provide for transcriptional and translational regulatory regions, a signal sequence and structural gene, which also may be readily excised and substituted, so as to allow for mixing and matching of regulatory regions, signal sequences and genes to evaluate regions for use in the expression of a desired peptide. Particularly, synthetic regions are provided which may be used with other synthetic regions or wild-type regions.

Plasmids are provided for screening Bacillus genomic sequences for regulatory regions, particularly promoters employing a structural gene secreting an enzyme which can produce a product which allows for visual detection.

18 Claims, 5 Drawing Sheets

```
5'-TAC TTGTTA  AAA ATT CGG AAT ATT TAT ACA ATA-
       -35    ◄────── N = 17 ──────►   -10

◄-NdeI-►
-TCATATG TTT CACATT GA  AAGGGG AGG AGA ATC-
                        Shine-Dalgarno -ATG AAA CAA CAA AAA CGG CTT TAC GCC CGA TCT-
 met⁺ lys⁺ gln gln lys⁺ arg⁺ leu tyr ala arg ser -18
-GTG ACG CTG TTA TTT GCG CTC ATC TTC TTG CTG-
 val thr leu leu phe ala leu ile phe leu leu ◄── PstI ──►
-CCT CAT TCT GCA G-3'
 pro his⁺ ser ala
```

REGULATORY REGION CLONING AND ANALYSIS PLASMID FOR BACILLUS

FIELD OF THE INVENTION

Plasmids are provided for isolating and evaluating regulatory regions of genes in Gram-positive bacteria, particularly Bacillus. Synthetic regulatory regions are provided associated with convenient restriction sites, whereby various cassettes can be prepared involving at least one of a promoter sequence, a ribosomal binding site sequence, and a signal sequence functional in Bacillus, where one or more of these regions may be substituted by the region to be evaluated. A plurality of restriction sites are provided for ease of substitution of one of the regions with a different region.

BACKGROUND OF THE INVENTION

In the use of genetic manipulation techniques in microorganisms, the genus Bacillus has, after *E. coli*, in recent years also formed the subject of extensive investigation. See, for example, Dubnau, in *Experimental Manipulation of Gene Expression*, Academic Press, (1983) 33-51 and Doi, *Biotechnology and Genetic Engineering* (1984) 2:126-155. Bacilli have now been used for a long time in the fermentation industry. Bacilli offer numerous advantages, such as good growth on inexpensive base materials, and in contrast to *E. coli*, do not produce any endotoxins. Furthermore, Bacilli are capable of secreting proteins into the growth medium, in particular, certain types of enzymes such as proteases and amylases, frequently produced in large amounts by Bacilli. These enzymes may be relatively inexpensively and conveniently isolated from the fermentation medium.

Because of the attractiveness of Bacilli as a host for the production of homologous or heterologous peptides, it is of substantial commercial interest to be able to make use of particular sequences associated with transcriptional and translational regulation, which would allow for efficient expression and secretion of the peptides of interest. There is, therefore, substantial interest in ways for isolating and analyzing these sequences from Bacillus or other sources, which would allow for the efficient screening of the sequences.

DESCRIPTION OF THE RELEVANT LITERATURE

Plasmids from *S. aureus* are capable of extrachromosomal maintenance in *B. subtilis* (Ehrlich, *Proc. Natl. Acad. Sci. USA* (1977) 74:1680-1682). Various prokaryotic and eukaryotic heterologous proteins have been cloned in *B. subtilis*, usually at low expression levels. See, for example, Kovacevic et al., *J. Bacteriol.* (1985) 162:521-528: Saunders et al., ibid. (1984) 157:718-726: Ohmura et al., *Third International Conference on Genetics and Biotechnology of Bacilli, Stanford, USA* (1984); Lundström, *FEBS Letters* (1984) 23:65-70, Palva et al., *Gene* (1983) 22:229-235: Lundström et al., *Virus Res.* (1985) 2:69-83: Hardy et al., *Nature* (1981) 293:481-483: Mosbach et al., *Nature* (1983) 302:543-545: Chang et al., *NSC Ser.* (1982) 4:254-261; Williams et al., *Gene* 1981) 16:199-206 and Flock et al., *Mol. Gen. Genet.* (1984) 195:246-251.

In order to arrive at an economically acceptable expression level, it is necessary to achieve improvements in the cloning system. In this context consideration can in particular be given to a modification of the promoter, in order to improve the transcription efficiency of the heterologous gene, a modification of the ribosomal binding site (Shine-Dalgarno), in order to improve the translation efficiency, and/or a modification of the signal sequence, in order to improve the secretion of the desired heterologous protein product.

Various proposals have been made for combining synthetic or naturally occurring promoters with a gene other than the wild-type gene. See for example Williams et al., *J. Bacteriol.* (1981) 146:1162-1165: Schoner et al., *Gene* (1983) 22:47-57, who describe plasmid pPL 603: Goldfarb et al., *Nature* (1981) 293:309-311 (plasmid pGR 71): Band et al., *Gene* (1983) 26:313-315 (plasmid pCPP 3-4): and Donelly and Sonnenshein, *J. Bacteriol.* (1984) 157:965-967 (plasmid pCED 6).

However, these plasmids have the disadvantage that they are fairly large and comprise only 1 or 2 promoter insertion sites. Moreover, they are almost all based on chloramphenicol acetyl-transferase as the indicator enzyme, and comprise an inducible Shine-Dalgarno sequence (pPL 603) or an inactive Shine-Dalgarno sequence (pGR 71). Consequently, promoters can be isolated only if a fusion protein is formed with the chloramphenicol acetyl-transferase, that is to say if a Bacillus Shine-Dalgarno sequence is also co-cloned and the reading frame is in phase with that of the chloramphenicol acetyl-transferase.

For discussion of the Shine-Dalgarno sequence and the initiation codon, see Hui et al., *EMBO J.* (1984) 3:623-629: De Boer et al., *DNA* (1983) 2:231-235: Band and Henner, *Biochem. Soc. Symp.* (1984) 48:233-245: and EPA 116411.

Concerns involved with evaluation of regulatory sequences have been expressed by Hall et al., *Nature* (1982) 295:616-618: Shpaer, *Nucleic Acids Res.* (1985) 13:275-289 and Tessier et al., ibid. (1984) 12:7663-7675.

Stanssens et al., *Gene* (1985) 36:211-213 describe the effect of alterations of the sequence upstream from the Shine-Dalgarno region: Iwakura et al., *J. Biochem* (1983) 93:927-930 describe the construction of plasmid vectors employing the dhfr gene: and Hosoya et al., *Agricultural and Biological Chemistry* (1984) 48:3145-3146, describe the construction of a promoter cloning vector in *P. aeruginosa*.

Ohmura et al., *J. Biochem* (1984) 95:87-93, describe a *B subtilis* secretion vector system employing the α-amylase promoter and signal sequence region: Enger-Valk et al., *Gene* (1981) 15:297-305 describe a vector for cloning of promoters: Tsoi et al., *Genetika* (Moscow) (1981) 17:2100-2104 describe the cloning and expression of promoter fragments of *B. thuringiensis* DNA in *E. coli* cells: Moran et al., *Mol. Gen. Genet.* (1982) 186:339-346 describe nucleotide sequences that signal the initiation of transcription and translation in *B. subtilis*; see also EPA 134048.

SUMMARY OF THE INVENTION

Novel DNA sequences and combinations of sequences are provided for the isolation of DNA fragments that can function as promoter in Bacilli. Said sequences are characterized by a structural gene, including a functional signal sequence, and a synthetic ribosomal binding site. The gene product encoded by the structural gene is, with the aid of the signal sequence, secreted by the host organism. Its activity can be easily assayed for, provided that upstream of the ribosomal binding site a DNA fragment is inserted, preferably using one of the available unique restriction sites. Said sequences are further characterized in that regulatory regions concerned with transcription, translation and secretion, and the structural gene itself can be conveniently exchanged by the presence of unique restriction sites bordering these regions. pPROM 54 is a promoterless plasmid useful in the screening of fragments for the presence of promoters in proper orientation and spacing.

BRIEF DESCRIPTION OF THE DRAWINGS

FIG. 1 depicts the nucleotide sequence of the promoter region, Shine-Dalgarno sequence, and signal sequence of *B. licheniformis* α-amylase with the predicted amino acid sequence of the signal sequence:

DESCRIPTION OF THE SPECIFIC EMBODIMENTS

Figure 2:
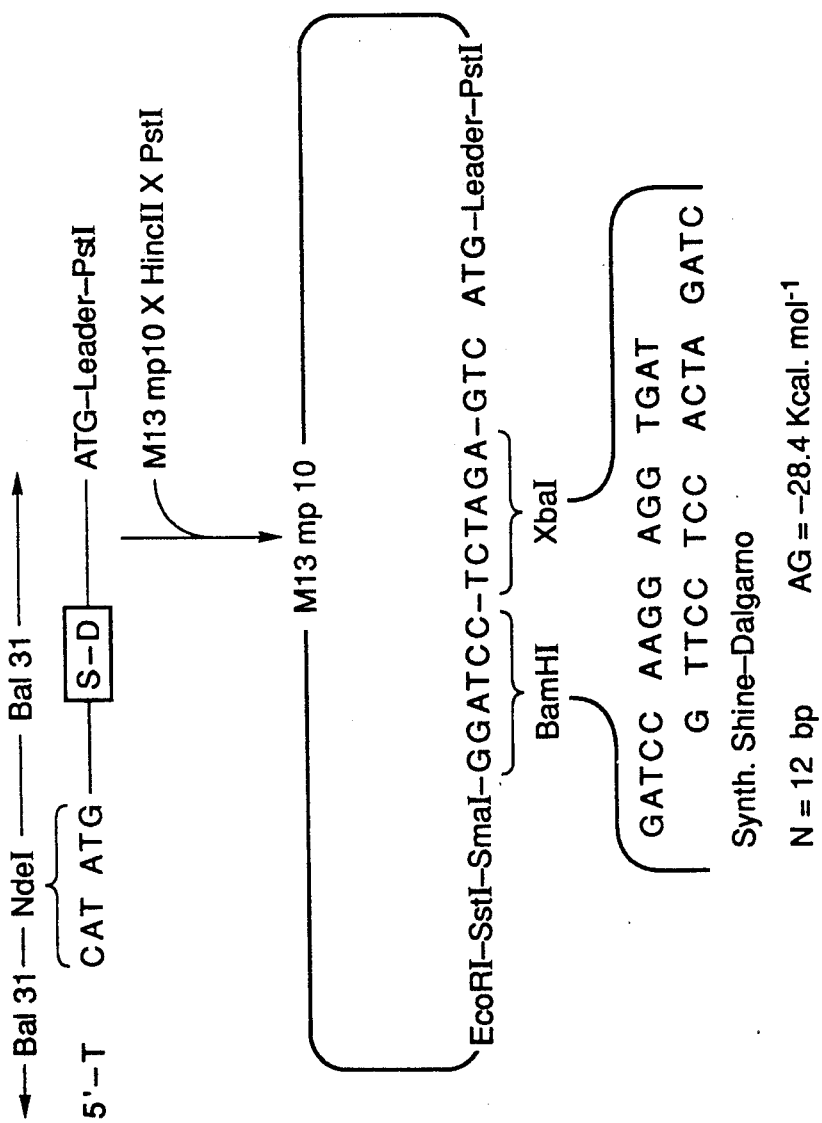
FIG. 2 depicts in diagrammatic form the removal of the natural α-amylase Shine-Dalgarno sequence and promoter sequence and the integration of the synthetic Shine-Dalgarno sequence in M13mp10.

Novel DNA sequences are provided in which a regulatory domain is provided. The domain allows for insertion and exchange of individual functional elements of the domain, as well as subunits of a functional element. The domain provides for transcriptional and translational regulatory elements, including elements affecting such regulation, such as operators, enhancers, activators, or the like. Of particular interest is a domain which provides for regulation of transcription, regulation of translation, both a ribosomal binding site and an initiation codon, a signal sequence for secretion and, as appropriate, a structural gene in reading phase with the signal sequence, which signal sequence may or may not include a processing signal for peptide cleavage.

The constructs allow for isolation of selected promoter sequences which bind to the Bacillus $\sigma^{55}$, $\sigma^{37}$, $\sigma^{32}$, $\sigma^{29}$, $\sigma^{28}$ or other RNA polymerases, provided with convenient restriction sites for introduction and excision from a vector. Also provided is a Shine-Dalgarno sequence with a plurality of convenient restriction sites so as to allow for introduction to and excision from a vector. A signal sequence for secretion is provided with convenient restriction sites for insertion and excision of the signal sequence, as well as insertion downstream and in reading frame with the signal sequence of a structural gene of interest.

A convenient Bacillus replication system is employed, such as the replication system pUB110. The vectors which are available will normally have a marker for selection, which marker allows for resistance to a cytotoxic agent such as an antibiotic, e.g. kanamycin, chloramphenicol, tetracycline, streptomycin, etc.; heavy metal, or the like: or complementation in an auxotrophic host. One or more markers may be present, particularly where a shuttle vector is employed, where the vector is capable of replication in two or more hosts. Conveniently, the vector may include a replication system for replication in two or more hosts. Conveniently, the vector may include a replication system for replication in *E. coli*, so as to allow for cloning and expansion of the DNA after each of the manipulative steps involved with the formation of the construct.

Suitable host microorganisms of the Bacillus species are *B. subtilis, B. licheniformis, B. amyloliquefaciens* and *B. stearothermophilus.*

At least one and preferably two of the subject sequences providing for a particular regulatory region or signal sequence are employed in combination with the sequence to be evaluated.

The first sequence to be considered is the promoter sequence. This region is involved with the binding of the $\sigma^X$-RNA polymerase wherein X intends any of the RNA polymerases indicated previously. The sequence may be synthetic or wild-type. One synthetic promoter will have the following sequence:

AATTCTTGACAAAGCTTCTCGAGACTGATATAATGAGCT
GAACTGTTTCGAAGAGCTCTGACTATATTAC

The subject synthetic sequence which is recognized by the $\sigma^{55}$-RNA polymerase has a number of significant features, allowing for the individual substitution of the $-10$ region or the $-35$ region by digestion with restriction enzymes HindIII or XhoI and SstI or digestion with EcoRI and HindIII or XhoI, respectively. The entire synthetic promoter may be substituted by digestion with EcoRI and SstI.

A second synthetic promoter, for the $\sigma^{37}$-RNA polymerase will have the following sequence:

AATTCAGGATTTATGAAGCTTGTCGAGGGAATTGTTTGAGCT
GTCCTAAATACTTCGAAGAGCTCCCTTAACAAAC

This sequence enjoys similar benefits as described for the $\sigma^{55}$-RNA polymerase promoter.

Other promoters which may be used to advantage include wild-type promoters, such as the wild-type promoter found in plasmid pPROM 3-4C., deposited at the CBS on November 5, 1985, under No. 699.85, where the promoter is a chromosomal promoter sequence derived from *B. licheniformis*. The above plasmid is derived from the plasmid pPROM 54, where the insertion of the *B. licheniformis* promoter results in an increase in α-amylase production in *B. subtilis* of 35%, compared with the plasmid pGB33 carrying the original promoter and Shine-Dalgarno sequences.

Another promoter derived from a bacteriophage promoter sequence is present in plasmid pPROM SP02, deposited at the CBS on Nov. 5, 1985, under No. 698.85. This plasmid is also derived from the plasmid pPROM 54, by insertion of a promoter sequence from the bacteriophage sequence derived from the plasmid pPL 608, which is described by Williams et al., supra. (1981). The insertion of the bacteriophage promoter results in an increase of α-amylase production in *B. subtilis* of 37% over the natural promoter.

These various promoter sequences may be substituted by any other promoter sequence, from any source, where it is intended to determine the efficiency of such promoter in a Bacillus host. Thus, promoter sequences, or portions of promoter sequences, either synthetic or natural, such as the $-10$ region or the $-35$ region consensus sequences may be incorporated for evaluation, by ligating such DNA sequences to one or more of the other sequences provided in accordance with this invention.

The next region of interest is the Shine-Dalgarno sequence or ribosome binding region. For this purpose, a synthetic region may be suitably employed having the following sequence:

```
GATCCAAGGAGGTGAT
    GTTCCTCCACTAGATC
```

The third sequence which is employed in the subject invention is the signal sequence of α-amylase, which may be conveniently joined to the region coding for the mature α-amylase or to a different gene resulting in a hybrid gene. A convenient restriction site is provided between the α-amylase signal sequence and the remainder of the α-amylase gene, so as to allow for substitution of the region coding for the mature α-amylase.

Each of the fragments which are employed provide for one or more restriction sites which allow for introduction and excision of the individual fragments. Thus, polylinkers or one or more restriction sites, desirably unique restriction sites, are present within and between the regions for convenient insertion or excision of sequences. Usually, the polylinker will have at least two restriction sites and usually not more than about six restriction sites, more usually not more than about four restriction sites, frequently unique restriction sites. Exemplary restriction enzyme recognition sites have been indicated previously.

The constructs of the subject invention may be prepared in accordance with conventional ways. The substitution by other sequences of the above regions may require modification of such other sequences. Modifications may include the use of linkers, adapters, in vitro mutagenesis, resection, repair, primer repair, or the like, where restriction sites may be introduced or removed, termini modified, etc. After each manipulation, it will usually be desirable to clone the new construct in a convenient host, such as *E. coli*, isolate the new construct and establish the presence of the correct sequence by restriction mapping, sequencing, or the like. Once the construct is completed, it may then be transferred to a vector capable of replication in a Bacillus host or a shuttle vector may be used for the construct, which allows for cloning in *E. coli* and direct transfer to the Bacillus host.

Of particular interest is the construction of a "fishing" plasmid for screening fragments of DNA for promoter regions functional in Bacillus. The fishing plasmid has two regions necessary for detection of a promoter region. The first region is a promoter screening region and the second region is a transformant selection region. The screening region comprises in the direction of transcription, a region of from about 4 to 100 bp having one or more unique restriction sites, usually not more than about 6, and lacking any transcriptional initiation activity. Downstream from the restriction site region is a ribosomal binding site region of from about 5 to 50 bp, including the non-coding nucleotides on either side of the Shine-Dalgarno consensus sequence. The sequence may be natural by occurring or synthetic. The ribosomal binding region is followed by a structural gene having a signal sequence for secretion. The structural gene expresses a product which can be readily detected by a simple chemical reaction without the possibility of significant interference from endogenous host materials. Of particular interest is α-amylase, which can be detected with a combination of amylose and iodine, where discharge of the color indicates the expression of α-amylase and the presence of a promoter in the restriction site region. Amylase can be conveniently present in the gel nutrient medium and clear halos are indicative of expression.

The second region provides for selection of transformants. This region will normally encode a gene imparting antibiotic resistance, so that only transformants having the plasmid will survive when grown in medium containing an otherwise cytotoxic amount of the antibiotic. Resistance to neomycin, tetracycline, penicillin, kanamycin, etc. may be provided with the appropriate genes.

Both the screening and selection regions will be joined to a replication system functional in Bacillus. Other functional regions may be present in the plasmid, such as a replication system for *E. coli* for cloning.

The fishing or screening method will involve fragmenting DNA from a Bacillus or other host e.g., virus, which may have regions capable of transcriptional initiation in Bacillus. The fragments may be mechanically produced or by using one or more restriction enzymes, particularly ones that have complementary ends to the restriction sites present in the restriction site region. Fragments as small as 20 bp and up to about 5 kbp, usually 2 kbp, may be obtained for screening, usually from about 50 bp to 1 kbp. The fragments are inserted into the fishing plasmid in accordance with conventional ways. The resulting plasmid library may then be transformed into a Bacillus host and the transformants selected by means of the antibiotic resistance.

Surviving Bacillus transformants may then be screened for active promoters by contacting clones with amylose and iodine and isolating those clones which become clear.

Transformation of Bacillus may be carried out in accordance with conventional ways. See, for example Anagnostopoulos and Spizizen, *J. Bacteriol.* (1961) 81:741–746. Transformants may then be selected in accordance with the nature of the marker.

By employing the subject constructs, structural genes may be evaluated for their ability to be expressed and secreted, where regulatory regions and the structural genes may be mixed and matched to provide for efficient production of the desired product. The production including secretion of a peptide may be determined and compared to other regulatory and functional sequences.

The following examples are offered by way of illustration and not by way of limitation.

EXAMPLE I

Isolation of Chromosomal DNA

Chromosomal DNA of *B. licheniformis*, strain T5, deposited at the CBS on July 6, 1983, under No. 470.83 (see EPA 134048) was isolated from 3 L of cultures which had grown overnight at 37° C., under aeration. The cells were centrifuged for 10 min. in a Sorvall GSA rotor at 10,000 rpm, suspended in 10 ml of sucrose-Tris buffer which contained 25% by weight of sucrose and 50 mM Tris-HCl at pH 8.0, and lysed by addition of 0.5 ml of lysozyme solution (20 mg/ml) and subsequently 15 min. incubation at 37° C. After addition of 2 ml of EDTA (0.5 M) and 5 min. incubation at 0° C., 1 ml of 20% by weight sodium dodecylsulfate (SDS) was added. Thereafter, the suspension was extracted with a 1:1 mixture of phenol and chloroform. The supernatant water layer was removed and carefully overlayered with 2 volume units of ethanol, after which the DNA could be isolated with the aid of a glass rod. After dissolution in distilled water to which 10 mg/ml ribonuclease had been added, the mixture was extracted with 1:1 phenol-chloroform, and the product precipitated with 2 parts of ethanol and resuspended in TE buffer (10 mM Tris-HCl, pH 8.0 and 1 mM EDTA).

EXAMPLE II

Isolation of Plasmid DNA

B. subtilis 1-85, containing plasmid pGB 33, deposited at the CBS under No. 466.83 (see EPA 134048), was cultured overnight in 1 L of minimal medium to which 10 mg/ml neomycin had been added. After centrifuging for 15 min. in a Sorvall model GSA rotor at 5,000 rpm and resuspending in 15 ml of sucrose-Tris, the cells were lysed and treated with EDTA and SDS (see Example I). After addition of NaCl to a final concentration of 1 M, the lysate was stored overnight at 4° C. and subsequently centrifuged for 15 min. at 12,500 rpm in a Sorvall type SS 34 rotor. The uppermost 70% (by volume) of the supernatant liquid was treated for 30 min. at 37° C. with 20 µg/ml of DNAse-free RNAse, and extracted with a 1:1 mixture of phenol-chloroform and subsequently with pure chloroform. The DNA was precipitated from the extracted supernatant liquid by addition of 0.2 part of 5 M NaCl and 0.25 part of 40% by weight polyethylene glycol 6000, followed by incubation at 4° C. overnight. After precipitation and centrifugation (30 min. at 12,500 rpm, Sorvall type SS 34, the DNA was resuspended in 2-3 ml of TE buffer (see Example I) and kept at pH 12.0 for 10-15 min. with the aid of 4N NaOH. Thereafter the pH was returned to 8.5 and the mixture was extracted with phenol. After precipitation with ethanol, the plasmid DNA was resuspended in a small volume of TE buffer.

EXAMPLE III

Oligonucleotide Synthesis

The following oligonucleotide sequences were synthesized with the aid of a Biosearch Synthesis Automation Machine and were purified by means of HPLC, extraction with phenol-chloroform (1:1) and precipitation with ethanol:

| (A) | 5'-GATCCAAGGAGGTGAT-3' |
|---|---|
| (B) | 5'-CTAGATCACCTCCTTG-3' |
| (C) | 5'-AATTCTTGACAAAGCTTC-3' |
| (D) | 5'-TCGAGAAGCTTTGTCAAG-3' |
| (E) | 5'-TCGAGACTGATATAATGAGCT-3' |
| (F) | 5'-CATTATATCAGTC-3' |
| (G) | 5'-AATTCAGGATTTATGAAGCTTC-3' |
| (H) | 5'-TCGAGAAGCTTCATAAATCCTG-3' |
| (I) | 5'-TCGAGGGAATTGTTTGAGCT-3' |
| (J) | 5'-CAAACAATTCCC-3' |

These oligonucleotides were used for synthesis of the following DNA sequences:

A. Synthetic Shine-Dalgarno Sequence

The oligonucleotides A and B were kinased by incubating a mixture of 5 µg of the two oligonucleotides for 1 hour at 37° C. with 60 µl of 1 mM ATP, 5 µl of 10 x kinase mix (0.5 M Tris-HCl pH 7.0, 0.1 M MgCl₂, 50 mM dithiothreitol, 1 mM spermidine, 1 mM EDTA) and 3 µl of T₄-kinase (Gibco, 10U/µl) in a total volume of 50 µl. The kinased oligonucleotides were subsequently annealed by 5 min. incubation at 100° C. followed by 30 min. incubation at 65° C. After purification with phenolchloroform (1:1) and precipitation with ethanol, the DNA was resuspended in a small volume of TE buffer.

B. Synthetic promoter-sequence recognized by σ⁵⁵-RNA polymerase

Analogously to the description under A, but starting from a mixture of the oligonucleotides C, D, E and F, a synthetic promoter sequence recognized by σ⁵⁵-RNA polymerase was obtained.

C. Synthetic promoter-sequence recognized by σ³⁷-RNA polymerase

Analogously to the description under A, but starting from a mixture of the oligonucleotides G, H, I and J, a synthetic promoter sequence recognized by σ³⁷-RNA polymerase was obtained.

EXAMPLE IV

Construction of a Shine-Dalgarno/signal sequence construct in plasmid pPROM 54

15 µg of pGB 33, isolated from B. subtilis 1-85 (see Example II) was cut with the restriction enzyme NdeI, of which the recognition site is located precisely between the promoter and the Shine-Dalgarno sequence of the B. licheniformis α-amylase gene, as may be seen from the sequence analysis (see FIG. 1). After extraction with phenol-chloroform (1:1) and precipitation with ethanol, the digested plasmid-DNA was resuspended in 59 µl of Bal31 mix (120 µl of 100 mM Tris-HCl pH 8.1, 72 µl of 100 mM MgCl₂, 72 µl of 100 mM CaCl₂, 120 µl of 1 M NaCl, 156 µl of H₂O and 1 µl of Bal31 exonuclease (Gibco 1.2 U/µl)). After 3.5 min. incubation at 15° C., the material was again extracted with phenolchloroform (1:1) and reprecipitated with ethanol. After resuspending, the DNA was digested with the restriction enzyme PstI, extracted with phenol-chloroform (1:1), precipitated with ethanol and resuspended in 20 µl of a ligase mix which contained 20 mM Tris-HCl pH 7.6, 10 mM MgCl₂, 10 mM dithiothreitol, 0.5 mM ATP, 1 µl E. coli phage M13mp10 (digested with the restriction enzymes HincII and PstI) and 1 µl of T₄ ligase (Boehringer 1 U/µl), after which ligation was carried out overnight at 4° C. (see FIG. 2).

Figure 3:
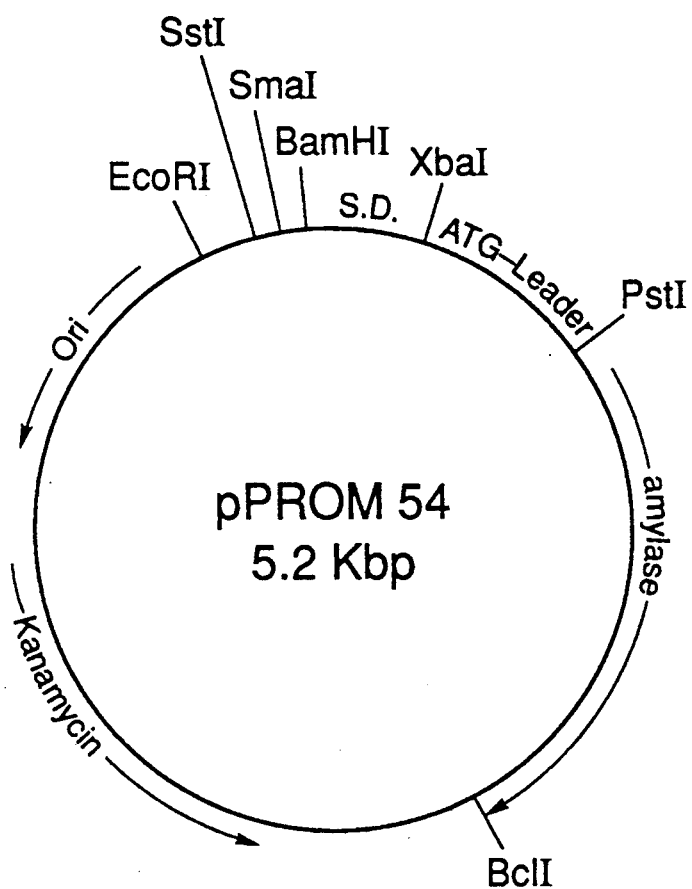
FIG. 3 depicts the plasmid pPROM 54.

After transformation and selection of white plaques in E. coli, a number of recombinant DNA phages were isolated and sequenced with the aid of the "dideoxychain terminator" method. In the recombinant most shortened by Bal31 (see FIG. 2) the synthetic Shine-Dalgarno sequence (see Example III) was inserted after digestion with the restriction enzymes BamHI and XbaI, after which the construct was sequenced. This fragment containing the Shine-Dalgarno sequence was subsequently excised with restriction enzymes EcoRI and PstI (see FIG. 2) and substituted for the EcoRI-PstI fragment carrying the original regulation signals of the B. licheniformis-α-amylase gene. The plasmid thus obtained, pPROM 54, has a size of about 5.2 kbp. The structure of the plasmid is shown in FIG. 3.

The plasmid pPROM 54 in B. subtilis 1A40 (amy⁻, lys⁻, met⁻, trp⁻) was deposited at the CBS on Nov. 5, 1985 under No. 696.85.

EXAMPLE V

Construction of pPROM plasmids which comprise chromosomal promoter sequences

5 μg of chromosomal DNA, isolated from *B. licheniformis* strain T5 (Example I) were cut with RsaI, HaeIII, AluI, HincII and EcoRV and, after purification with phenol-chloroform and precipitation with ethanol, were ligated to 1 μg of pPROM 54 (Example IV), restricted with SmaI. Another portion of chromosomal DNA from *B. licheniformis* strain T5 was digested with EcoRI under Eco* conditions, purified, precipitated and ligated to 1 μg of pPROM 54, linearised with EcoRI. The ligated mixtures were transformed into *B. subtilis* 1A40 (amy−, lys−, met−, trp−) using the method described by Anagnostopoulos and Spizizen, *J. Bacteriol.* (1981) 81:741-746. Transformants were first selected for neomycin/kanamycin resistance on minimal agar plates to which 0.02% (w/v) of casamino acids (Difco) and 10 μg/ml neomycin were added.

These transformants were subsequently analyzed for the presence of a promoter sequence by selection in respect of the capacity achieved for the synthesis of α-amylase, which was done by looking for halos after having poured a solution of 0.6% (w/v) of KI and 0.3% (w/v) of $I_2$ over the plates. The transformants thus selected were used for fermentation production of α-amylase in comparison with production under the influence of the native α-amylase regulatory region. The selected transformants were also used as the source for recombinant DNA plasmids.

One of the selected transformants comprised the plasmid pPROM 3-4C. This plasmid in *B. subtilis* 1A40 (amy−, lys−, met−, trp−), was deposited at the CBS on Nov. 5, 1985 under No. 699.85.

EXAMPLE VI

Construction of pPROM plasmids which comprise bacteriophage promoter sequences

5 μg of pPL 608 carrying an SP02 phage promoter fragment of 280 bp (Williams et al. *J. Bacteriol.* (1981) 146:1162-1165), were cut with EcoRI and, after purification and precipitation, were ligated to 1 μg of pPROM 54, linearized with EcoRI. The ligated mixture was transformed into *B. subtilis* 1A40 (amy−, lys−, met−, trp−). The transformants obtained were selected in the manner described in Example V. The selected transformant comprised the plasmid pPROM SP02. This transformant was used for fermentative production of α-amylase in comparison with the production under the influence of the native α-amylase gene and also used as a source for the recombinant plasmid pPROM SP02.

The plasmid pPROM SP02 in *B. subtilis* 1A40 (amy−, lys−, met−, trp−) was deposited at the CBS on Nov. 5, 1985 under No. 698.85.

EXAMPLE VII

Construct PROM plasmids which comprise synthetic promoter sequences

Figure 4:
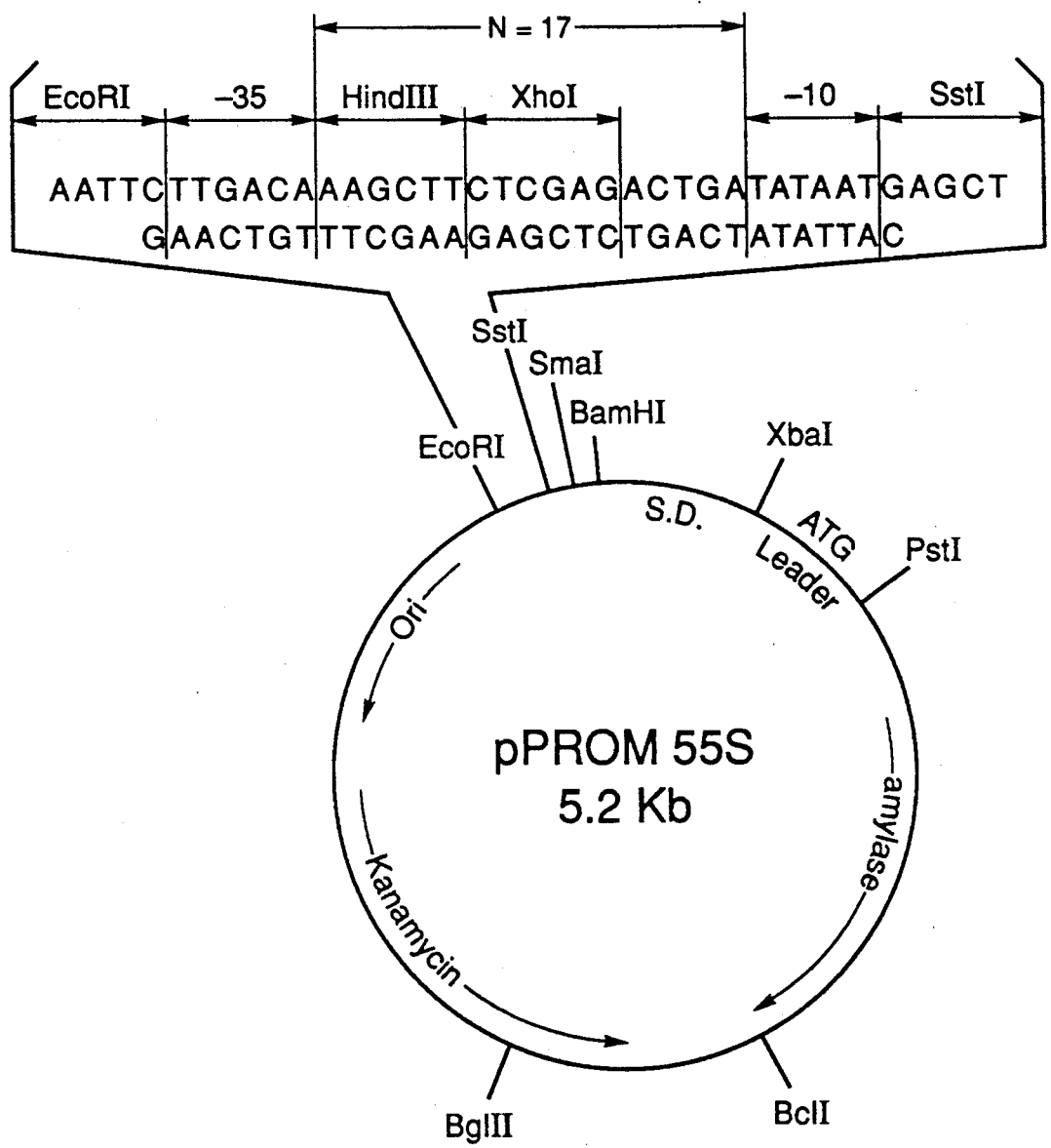
FIG. 4 depicts the plasmid pPROM 55s.

5 μg of the synthetic promoter obtained by purification and annealing of the oligonucleotides C, D, E and F (see Example III) were ligated to 1 μg of pPROM 54 and digested with Eco RI and Sst I (see FIG. 4.) The ligated mixture was transformed into *B. subtilis* 1A40 (amy−, lys−, met−, trp−). The transformants obtained were selected in the manner described in Example V. The selected transformant comprised the plasmid pPROM 55s. The transformant was used for fermentative production of α-amylase in comparison with the production under the influence of the native α-amylase gene, and also as a source for the recombinant plasmid pPROM 55s.

The plasmid pPROM 55s in *B. subtilis* 1A40 (amy−, lys−, met−, trp−) was deposited at the CBS on Nov. 5, 1985 under No. 697.85.

Figure 5:
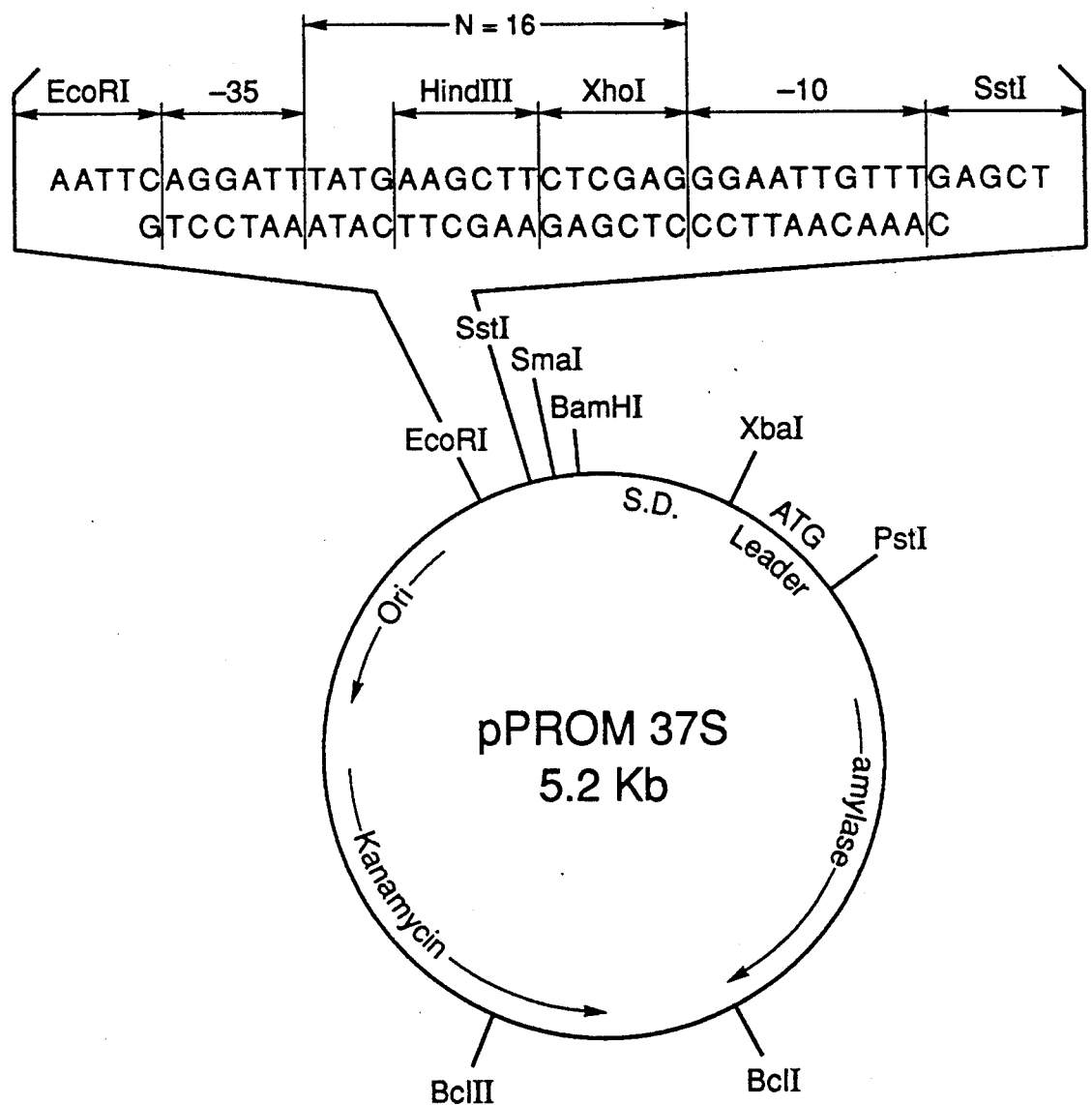
FIG. 5 depicts the plasmid pPROM 37s.

Analogously to this procedure, but starting from the synthetic oligonucleotides G, H, I and J (see Example III), a Bacillus 1A40 transformant containing the recombinant plasmid pPROM 37S, was obtained, which plasmid differs from pPROM 55s in respect of the synthetic promoter sequence (compare FIGS. 4 and 5).

EXAMPLE VIII

Fermentative Production of α-Amylase with the aid of genetically manipulated Bacillus subtilis strains The *B. subtilis* strains obtained after genetic manipulation as described in Examples V, VI and VII, and also the *B. subtilis* strain with the starting plasmid pGB 33, were cultured for 5 days at 37° C. in a liquid heart infusion medium made up with 0.4% of Zulkowski starch. The α-amylase was isolated and purified in accordance with standard procedures. The quantities of α-amylase produced, in comparison with the original *B. subtilis* strain having the starting plasmid pGB 33 (bearing the unmodified α-amylase gene) are shown in Table I.

TABLE I

| Origin of Promoter | | Clone No. | α-amylase production (TAU/ml) | % compared with control |
|---|---|---|---|---|
| *B. lich.* chromosomal DNA | x Rsa I | pPROM 1.1 | 48.2 | 116 |
| | x Rsa I | pPROM 2.6 | 44.3 | 107 |
| | x Alu I | pPROM 11.1 | 47.0 | 113 |
| | x Alu I | pPROM 14.3 | 43.4 | 117 |
| | x Hinc II | pPROM 17.4 | 39.7 | 96 |
| | x Hinc II | pPROM 17.5 | 36.4 | 88 |
| | x Hinc II | pPROM 17.6 | 43.5 | 105 |
| | x EcoRV | pPROM 23.25 | 45.5 | 110 |
| | x EcoRV | pPROM 23.26 | 49.3 | 119 |
| | x EcoRI* | pPROM 3-4C | 55.8 | 135 |
| pL 608 DNA | x EcoRI | pPROM SPO2 | 56.8 | 137 |
| Synthetic DNA | | pPROM 37s | 39.3 | 95 |
| | | pPROM 55s | 33.1 | 80 |
| Control | | pGB 33 | 41.4 | 100 |

In accordance with the subject invention, functional sequences can be readily isolated and evaluated by substitution or insertion of regulatory regions, signal sequences, or structural genes into a designed construct. The resulting constructs may then be introduced into a Bacillus host and the efficiency of expression and secretion determined. In this manner, Bacillus libraries or libraries from other hosts which may have regulatory regions functional in Bacillus may be screened for their use in Bacillus. Thus, promoters, ribosomal binding sites and signal sequences may be evaluated from a wide variety of hosts, such as viruses, microorganisms, and the like.

Although the foregoing invention has been described in some detail by way of illustration and example for purposes of clarity of understanding, it will be obvious that certain changes and modifications may be practiced within the scope of the appended claims.

What is claimed is:

1. A plasmid capable of replication in Bacillus useful for evaluating regulatory or signal sequences for expression of a hybrid gene, said plasmid comprising:
a domain comprising at least one unique restriction site and as elements for substitution, in the direction of transcription,
(1) a promoter region functional in Bacillus selected from the group consisting of:
(i) the *B. licheniformis* promoter sequence from pROM3-4C,
(ii) the bacteriophage promoter of pROM SP02,
(iii) the −10 or −35 region of a synthetic promoter comprising at least a portion of the sequence

AATTCTTGACAAAGCTTCT
GAACTGTTTCGAAGAG

GAGACTGATATAATGAGCT
CTCTGACTATATTAC and (iv) the −10 or −35 region of a synthetic promoter comprising at least a portion of the sequence

AATTCAGGATTTATGAAGCTTCT
GTCCTAAATACTTCGAAGA

TCTCGAGGGAATTGTTTGAGCT
AGAGCTCCCTTAACAAAC;

(2) a ribosomal binding site, with the proviso that when said promoter region is absent, said ribosomal binding site is synthetic and consists essentially of:

GATCCAAGGAGGTGAT
GTTCCTCCACTAGATC; and (3) a signal sequence functional in Bacillus; wherein unique restriction sites are located between the −10 and −35 consensus sequences of any synthetic promoter region, between the promoter region and the ribosomal binding site, proximal to the initiation codon and at the 3'-terminus of the signal sequence; wherein at least two of said elements are not naturally linked; and wherein when one of said elements other than said signal sequence is unique restriction site, said signal sequence is the α-amylase signal sequence joined in reading frame to a structural gene encoding mature α-amylase.

2. A plasmid according to claim 1 wherein said regulatory domain comprises at least one of the following: a ribosomal binding site which comprises at least one of (A) 5'-GATCCAAGGAGGTGAT-3' or
(B) 5'-CTAGATCACCTCCTTG-3', and a promoter which comprises at least one of (C) 5'-AATTCTTGACAAAGCTTC-3'
(D) 5'-TCGAGAAGCTTTGTCAAG-3'
(E) 5'-TCGAGACTGATATAATGAGCT-3'
(F) 5'-CATTATATCAGTC-3'
(G) 5'-AATTCAGGATTTATGAAGCTTC-3'
(H) 5'-TCGGAAGCTTCATAAATCCTG-3'
(I) 5'-TCGAGGGAATTGTTTGAGCT-3' or
(J) 5'-CAAACAATTCCC-3'.

3. A plasmid according to claim 1, wherein said promoter is replaced with a sequence which includes at least three unique restriction sites.

4. A plasmid according to claim 1, wherein said promoter specifically binds to the $\sigma^{55}$-RNA polymerase.

5. A plasmid according to claim 4, wherein said promoter has the sequence:

AATTCTTGACAAAGCTTCTCGAG
GAACTGTTTCGAAGAGCTC

ACTGATATAATGAGCT
TGACTATATTAC.

6. A plasmid according to claim 1, wherein said promoter specifically binds to the $\sigma^{37}$-RNA polymerase.

7. A plasmid according to claim 6, wherein said promoter has the sequence:

AATTCAGGATTTATGAAGCTTC
GTCCTAAATACTTCGAAG

TCGAGGGAATTGTTTGAGCT
AGCTCCCTTAACAAAC.

8. A plasmid according to claim 1, wherein said plasmid comprises the replication system of pUB110.

9. A plasmid according to claim 1, wherein said plasmid comprises at least one gene imparting antibiotic resistance to Bacillus.

10. A plasmid according to claim 1, wherein said ribosomal binding site has the sequence:

GATCCAAGGAGGTGAT
GTTCCTCCACTAGATC.

11. A plasmid according to claim 1, consisting essentially of pPROM 54, pPROM SP02, pPROM 37s, pPROM s, pPROM 1.1, pPROM 2.6, pPROM 11.1, pPROM 14.3, pPROM 17.4, pPROM 17.5, pPROM 23.25, pPROM 23.26, or pPROM 3-4C.

12. A plasmid according to claim 11, wherein at least one but not all of the elements are substituted by a different sequence having the same function as the element that has been substituted.

13. A plasmid according to claim 1, comprising in reading phase with said signal sequence a structural gene joined to said signal sequence.

14. A Bacillus host comprising a plasmid according to claim 1.

15. A *Bacillus subtilis* host comprising a plasmid according to claim 1.

16. A method for determining the efficiency of one or more functional elements in the production of a peptide in a Bacillus host, said peptide being non-lethal to said host, said method comprising: growing said host in an appropriate nutrient medium, said host comprising a plasmid capable of replication in Bacillus having a domain comprising as elements for substitution in the direction of transcription, wherein at least one, but not all, of the elements for substitution is substituted by at least one of said functional elements that has the same function as the element for substitution that is being substituted, said elements for substitution consisting essentially of:

(1) a promoter region function in Bacillus selected from the group consisting of:
i) the *B. licheniformis* promoter sequence from pROM3-4C, ii) the bacteriophage promoter of pROM SP02,
iii) the −10 or −35 region of a synthetic promoter comprising at least a portion of the sequence

AATTCTTGACAAAGCTTCTC
GAACTGTTTCGAAGAG

GAGACTGATATAATGAGCT
CTCTGACTATATTAC, and iv) the −10 or −35 region of a synthetic promoter comprising at least a portion of the sequence

AATTCAGGATTTATGAAGCTTCT
GTCCTAAATACTTCGAAGA

TCTCGAGGGAATTGTTTGAGCT
AGAGCTCCCTTAACAAAC (2) a ribosomal binding site, with the proviso that when said promoter region is absent, said ribosomal binding site is synthetic and consists essentially of:

GATCCAAGGAGGTGAT
GTTCCTCCACTAGATC, and (3) a signal sequence functional in Bacillus; with unique restriction sites between the −10 and −35 consensus sequences of any synthetic promoter region, between the promoter region and the ribosomal binding region, between the promoter region and the ribosome binding site, proximal to the initiation codon and the 3'-terminus of the signal sequence, wherein a structural gene is in reading phase with said signal sequence; and determining the amount of said peptide produced in comparison with the amount of peptide produced under comparable conditions with said domain prior to any substitution with said functional elements.

17. A method for detecting the presence of a sequence capable of initiating transcription of a DNA sequence encoding a peptide in a Bacillus host, said peptide being non-lethal to said host, said method comprising:
fragmenting DNA from a host having transcriptional initiation regions to less than about 5 kbp to produce DNA fragments;
inserting said DNA fragments into a plasmid capable of replication in Bacillus and having a domain comprising in the direction of transcription,
(1) a unique restriction site
(2) a ribosomal binding site having the nucleatide sequence GATCCAAGGAGGTGAT
GTTCCTCCACTAGATC; and (3) a signal sequence function in Bacillus; and
(4) a structural gene encoding a product which is readily detectable by a chemical reaction and which is in reading phase with said signal sequence; and
transforming Bacillus cells with said plasmid to produce transformants and selecting for transformants by means of a selectable marker carried on said plasmid; and
screening transformants for secretion of said product by means of said chemical reaction to determine the presence of a fragment at said restriction site having transcriptional initiation capability.

18. A method according to claim 17, wherein said structural gene encodes α-amylase.

* * * * *